United States Patent [19]

Rosen

[11] Patent Number: 5,071,345
[45] Date of Patent: Dec. 10, 1991

[54] DENTAL CROWN ANALOG FOR ORTHODONTIC ANCHORAGE

[76] Inventor: David B. Rosen, 9 Trodden Path, Lexington, Mass. 02173

[21] Appl. No.: 400,881

[22] Filed: Aug. 30, 1989

[51] Int. Cl.$^5$ .......................... A61C 3/00; A61C 8/00
[52] U.S. Cl. ....................................... 433/17; 433/24; 433/173
[58] Field of Search ................. 433/173, 174, 17, 24, 433/10, 191, 196

[56] References Cited

U.S. PATENT DOCUMENTS

| | | | |
|---|---|---|---|
| 851,578 | 4/1907 | West | 433/191 |
| 1,014,348 | 1/1912 | Todd | 433/191 |
| 1,303,223 | 5/1919 | Wall | 433/196 |
| 1,507,024 | 9/1924 | Monson | 433/191 |
| 2,644,231 | 7/1953 | Brennan | 433/173 |
| 2,697,278 | 12/1954 | Kohler | 433/191 |
| 3,526,961 | 9/1970 | Kesling | 433/17 |
| 3,866,221 | 2/1975 | Valen | 433/174 X |
| 4,024,638 | 5/1977 | Linkow et al. | 433/176 |
| 4,318,696 | 3/1982 | Kasama et al. | 433/173 |
| 4,344,757 | 8/1982 | Streel | 433/173 |
| 4,522,596 | 6/1986 | Ashkinazy | 433/173 |
| 4,713,003 | 12/1987 | Symington et al. | 433/173 |
| 4,738,062 | 4/1988 | Dickey | 433/173 X |
| 4,756,689 | 7/1988 | Lundgren et al. | 433/173 |
| 4,758,162 | 7/1988 | Dobbs | 433/191 X |
| 4,812,120 | 3/1989 | Flanagan et al. | 433/173 |
| 4,854,872 | 8/1989 | Detsch | 433/173 |

FOREIGN PATENT DOCUMENTS 89-03200  4/1989  World Int. Prop. O. .......... 433/173

Primary Examiner—Robert P. Swiatek
Assistant Examiner—Nicholas D. Lucchesi
Attorney, Agent, or Firm—Alfred H. Rosen

[57] ABSTRACT

A dental crown analog suitable for orthodontic anchorage mates with an endosseous dental implant fixture to provide such anchorage at an edentulous site. The crown analog is tapered down toward the transverse dimensions of the implant fixture above the gun line, to minimize the accumulation of bacterial plaque, and to facilitate cleaning by the patient during the process of orthodonitc therapy. A standard abutment fixed to the implant fixture may be used with a dental crown overlay fitted over the abutment to provide a choice of crown sizes and shapes.

16 Claims, 1 Drawing Sheet

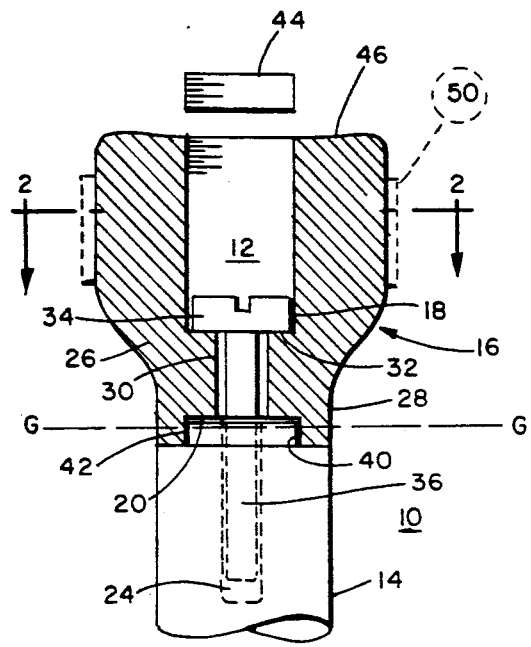
FIG. 1
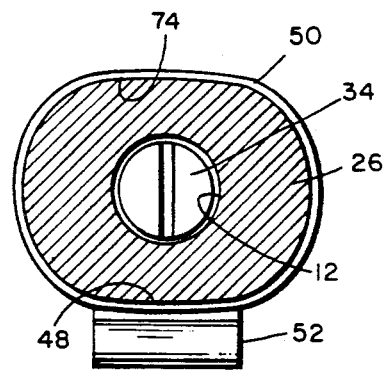
FIG. 2
FIG. 3
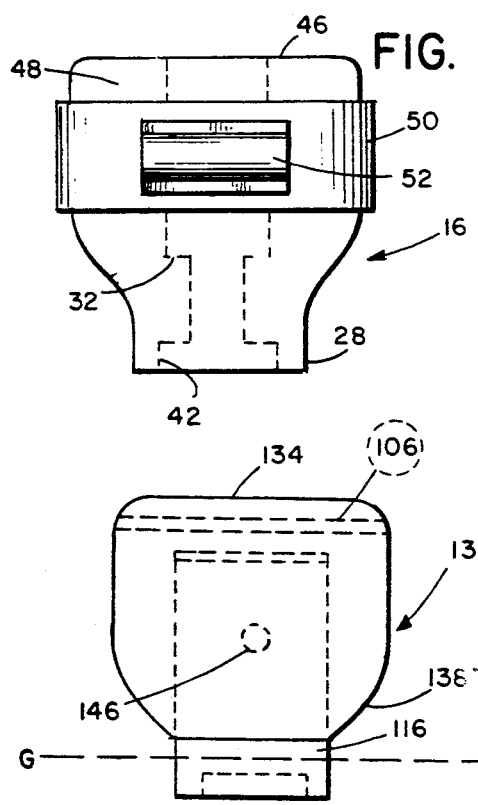
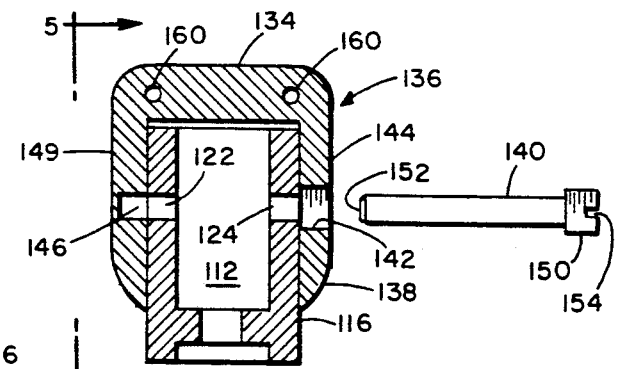
FIG. 4
FIG. 5

DENTAL CROWN ANALOG FOR ORTHODONTIC ANCHORAGE

INTRODUCTION

This invention relates in general to the dental field of orthodontics, and more particularly to a dental crown analog for orthodontic anchorage to a dental implant fixture in a patient who is edentulous at the site where such anchorage is desired. This invention is related to the invention of my co-pending application for U.S. patent Ser. No. 07/385,193 filed July 26, 1989, the disclosure of which is incorporated herein by reference.

BACKGROUND OF THE INVENTION

In one class of systems used in orthodontic practice arch-wires cooperating with brackets affixed to buccal or lingual surfaces of teeth are used to adjust the relative positions of teeth in a dental arch with appropriate forces applied over time to individual teeth in the arch. These wires are anchored at their ends to tubes, hooks and the like affixed to the patient's molars, pre-molars, or other suitable teeth. Elastics and ligature threads are also in orthodontic use and these, too, cooperate with traction hooks and buttons affixed to surfaces of patient's teeth.

In cases of patients who have lost their molars or premolars, or otherwise lack suitable anchorage, the use of molar tubes, hooks, buttons and the like has not been available to orthodontists. However, now that the art of dental implantology is developed to provide a variety of artificial root fixtures, notably the endosseous implant fixture, an opportunity exists to fill that need for partially edentulous patients.

It has only recently been ascertained that an endosseous dental implant fixture can be used to enhance dental anchorage in orthodontics. A report by Douglass, J. B. and Killiany, D. M., entitled "Dental Implants used as Orthodontic Anchorage" J. Oral Implantology 13 No. 1 pp. 28–32, 1987 describes experiments with rats using implanted posts extending 3 mm. coronally to which ligature wire was tied. A later article by Kraut, R. A. Hammer, H. S. and Wheeler, J. J., entitled "Use of Endosteal Implants as Orthodontic Anchorage" Compendium of Continuing Education in Dentistry 9 No. 10 pp. 796–801, 1988 reports several cases in which endosteal implants were used as orthodontic anchors in humans. In each case cast crown forms were custom fabricated to accept orthodontic molar bands, and those crowns were affixed to the implants. Another article by Shapiro, P. A. and Kovich, V. G., entitled "Use of Implants in Orthodontics" Dental Clinics of North America 52 No. 3 pp. 539–550, 1988 further confirms the utility of a successful endosseous implant to facilitate orthodontic therapy.

GENERAL NATURE OF THE INVENTION

A dental implant fixture in the class of endosseous implants consists essentially of an elongated body implanted in the patient's jawbone and having an elongated socket for receiving a fitting or fittings which fix a prosthodontic restoration on the implanted fixture. Commonly, the socket is an internally-threaded receiving bore, and the restoration is fixed to the implanted fixture with a bolt threaded into that bore. Other forms of dental implants are in use, and a wide variety of materials are used in making them. This invention is disclosed in connection with the endosseous implant fixture as currently known to be in use, as a best mode now known to practice the invention. It will be understood that the invention is not limited to the details of the illustrative disclosure; to the contrary, the invention is intended for use with any and all substitutes for natural tooth structures that are capable of providing the required anchorage, whether presently known or made available in the future.

Control of dental plaque, consisting of bacteria, is a very important factor in the general health of the soft and hard tissues which support the teeth. If bacterial plaque is allowed to accumulate in the gingival sulcus it will result in gingival inflammation and bone loss in the affected areas. This becomes particularly important during the process of orthodontic therapy. The mechanical brackets, bands and other attachments serve as plaque-retentive areas that require extra effort on the part of the patient in order to keep them clean and prevent periodontal disease. This invention incorporates a design that is contoured to provide a surface that is even with, and the same size as, the underlying implant in order to minimize plaque retention. The contour then tapers in a smooth fashion in order to make it more readily cleansible. Orthodontic therapy typically takes 1-2 years, during which time it is desirable to maintain the highest level of oral hygiene.

During the process of orthodontic therapy, there is a constant process of remodeling of the bone surrounding the teeth being moved. Bone is resorbed on the pressure side of the teeth being moved and bone is deposited on the tension side of the same teeth. Bacterial plaque can interfere with this process. The presence of inflammation, which is in response to the bacterial deposits, inhibits the process of bony deposition during tooth movement. This results in a tooth being moved and bone being resorbed on the pressure side with no subsequent repair at the site from where the tooth is being moved. The result can be disastrous if the mouth is allowed to be unclean and unhealthy. When a dental implant is involved, this accumulation of bacterial plaque can result in loss of osseointegration and a subsequent loosening and failure of the implant. This invention is designed to allow an environment that is easily cleaned by the patient during the process of orthodontic therapy and to minimize the accumulation of bacterial plaque.

The present invention teaches a new way to use dental implants for orthodontic anchorage. Generally according to the invention a standardized prefabricated dental crown analog, designed and intended as a component for dental implant systems, provides orthodontic anchorage for archwires, ligatures, elastics and the like. The invention provides, in one of its preferred forms, a dental crown analog for orthodontic anchorage which comprises a tubular passage having at a first end an internal flange providing a shoulder for the head of a bolt by which to attach the crown analog to an endosseous implant fixture of the type having an internally-threaded receiving bore. Exteriorly, the first end of the crown analog is shaped to mate with the gingival end of the implant fixture in the same manner as components that are in use with that fixture for prosthodontic restoration purposes. Between the flange and the occlusal end of the crown analog the side walls of the crown analog flare out to mimic the shape of a tooth normally found in the site of the implanted dental implant fixture. Preferably the crown analog is tapered supragingivally short of the gingival margin to minimize plaque accumulation near the gingival margin during the orthodontic therapy. Crown analogs according to the invention can be provided in sizes and shapes to mimic molars, pre-molars and other teeth. Crown analogs of molars can be provided with integral passages for anchoring the ends of archwires, as well as external dimensions specifically adapted to accept ortho-bands with molar tubes and other brackets and fixtures attached. The invention allows orthondontic anchoring devices, e.g: a molar tube, to be fitted to a patient in the same manner as to a natural tooth. Dental crown analogs according to the invention can be positioned rotationally around the axis of the socket or receiving bore in the patient's osseointegrated implant fixture.

DETAILED DESCRIPTION OF THE DRAWINGS

The invention is disclosed in fuller detail with reference to the accompanying drawings, in which:

FIG. 1 illustrates in section between lingual and buccal aspects a dental crown analog according to the invention;

FIG. 2 is a sectional view from the occlusal aspect taken along line 2—2 of FIG. 1;

FIG. 3 is a buccal view of the dental crown analog shown in FIG. 1;

FIG. 4 is a sectional view between lingual and buccal aspects of another embodiment of the invention; and FIG. 5 is a lingual side view take from line 5—5 of FIG. 4.

As appears in FIG. 1, a patient whose lower jaw 10 is edentulous at the site illustrated has an endosseous implant fixture 14 fixed in the lower jaw 10 at the site of a missing tooth. The implant fixture 14 is shown having an internally-threaded receiving bore 24. The dental crown analog 16 of the invention that is illustrated consists primarily of a body 26 with a tubular passage 12 having at a first end 18, near the lower, or gingival, end 28 of the body 26 as shown in the drawing, an internal flange 30 providing a shoulder 32 for the head 34 of a bolt 36 by which to attach the crown analog 16 to the implant fixture 14. In order to prevent rotation of the crown analog 16 relative to the implant fixture 14, around the axis of the receiving bore 24, the gingival end 20 of the implant fixture and the gingival end 28 of the crown analog 16 may be provided with interlocking male and female anti-rotation fittings 40, 42, respectively. These may be a hexagonal socket 42 and a hexagonal projection or boss 40, but they may be reversed, and they may be changed in shape, as desired. An ortho-band 50 may be fixed around the side surfaces of the crown analog 16, as is indicated in dashed lines in FIG. 1.

Referring now to FIGS. 2 and 3, the ortho-band 50 may carry a molar tube 52 fixed to a side of the ortho-band. This is one example of a standard component used in orthodontic therapy that can be used with the invention in the same way that the component is used with a natural tooth.

In use of the invention as illustrated in FIGS. 1, 2 and 3, the surface 48 of the crown analog 16 is the buccal surface and the opposite surface 74 is the lingual surface. The outer shape of the crown analog will mimic the shape of a molar, a pre-molar, or another tooth, as needed. The crown analog shown in these figures is contoured in cross-section to approximate the shape of a molar, so that the buccal surface 48 may be generally wide and flat. A cap-screw 44 may be used to close the access opening into the passage 12 through the occlusal surface 46 of the crown analog 16.

The crown analog 16 can be used to support a wide variety of fittings and attachments of use to orthodontists. Examples are hooks, lingual buttons, and combined molar tubes and hooks. The crown analog may be made of a dental material, or of a metal covered with a dental material, to which orthodontic therapy fittings can be attached with a cement or other bonding material in the same manner as such fittings are attached to natural teeth.

The crown analog 16 is intended to be compatible with, and capable of being an integral part of, a dental restoration plan for a patient who is partially edentulous, and who may intend to acquire a full-mouth restoration following orthodontic therapy. To this end the crown analog 16 is designed and intended to be useful with a dental implant fixture that may ultimately be used to support a prosthodontic restoration. To minimize plaque accumulation during orthodontic therapy, the body 26 is preferably supragingivally tapered toward its gingival end 28, to the dimensions of the implant fixture 14. This taper is completed above the gum line G—G, indicated in FIG. 1. The gingival end 28 of the body 26 can be mated to the implant fixture 14 under the gum line G—G.

FIGS. 4 and 5 illustrate an embodiment of the invention that makes use of a standard abutment 116 which is similar to the abutment 16 which is described and claimed in my above-referenced co-pending application. This abutment is a generally tubular body having a passage 112 similar to the passage 12 in the crown analog 16, and two opposite holes 122 and 124 in its side walls which are useful for purposes described in my co-pending application. My present invention uses these two holes to fix to the abutment 116 an overlay crown analog 136 which may serve the same uses and purposes as the crown analog 16 of FIGS. 1, 2, and 3. This crown analog may be made of or covered with any dental material to which orthodontic cements and bonding materials will adhere substantially the same as they adhere to patients' natural teeth. Plastics materials, such as dental acrylic materials, are suitable for this purpose. The occlusal surface 134 of the overlay crown analog 136 is closed. The lower, or gingival, end 138 of this analog is tapered toward the standard abutment 116 supragingivally, providing the same prophylactic benefits as the tapered crown analog 16. To fix the overlay crown analog 136 to the abutment 116 a bolt or pin 140 is fitted through an internally-threaded hole 142 that passes through one side-wall (e.g: the buccal wall) 144 of the overlay 136, through the hole 124, across the passage 112, through the hole 122 of the abutment 116, and into a recess 146 in the inner surface 148 of the opposite (labial) side-wall 149 of the overlay crown analog 136. The internally-threaded hole 142 is axially in register with abutment hole 124, and the recess 146 is axially in register with abutment hole 122. The internally-threaded hole 142 is slightly larger in diameter than the abutment hole 124. The head 150 of the bolt or pin 140 is also slightly larger in diameter than the remainder of the bolt or pin 140, and is externally-threaded to mate with the internally-threaded hole 142. The head 150 is axially shorter than the internally-threaded hole 142, so that when the bolt or pin 140 is fully seated with its end 152 in the recess 146 the head will be completely within the internally-threaded hole 142. A screwdriver slot 154, or equivalent, is provided in the head 150. When the overlay crown analog 136 is fixed on the standard abutment 116, an ortho-band (not shown) may be fitted around it.

In use of the FIGS. 4 and 5 embodiment of the invention, the standard abutment 116 is installed in the patient's mouth, and the orthodontist can affix the overlay crown analog 136 to it. This embodiment of the invention offers an additional possibility, via integral tubular passages 160 running from the mesial aspect to the distal aspect in the overlay crown analog 136, near the occlusal surface 134, which can be used to anchor the ends of archwires without requiring a separate orthodontic fixture such as a molar tube. This embodiment of the invention may also be used for the more general purpose of fitting a temporary crown to a patient. The degree of precision that might be required in a permanent prosthodontic restoration is not necessarily required for the purpose of fitting a temporary crown to the abutment 116. Looseness in the fit between the overlay crown analog 136 and the abutment 116 may, if desired, be filled with a temporary cement.

I claim:

1. For use in the mouth of a patient having an endosseous dental implant fixture or the like installed in the patient's jawbone at an edentulous site, a prefabricated dental crown analog having an exterior size and contour to approximate the dimensions and shape of a natural tooth at said site, and an orthodontic wire anchor consisting essentially of hollow tubular means providing an intergral passage extending measially-distally through said analog closer to one of the exterior buccal or lingual surfaces than to the center thereof, for passage of an orthodontic wire through said passage whereby said wire may be anchored with said crown analog.

2. A dental crown analog according to claim 1 in combination with an abutment post, means to affix said post at a gingival end to said implant fixture, and means to affix said crown analog over the supragingival end of said post.

3. A dental crown analog and abutment post combination according to claim 2 in which said crown analog has a bore opening through its gingival end into which said supragingival end of said post fits, said crown analog when fixed on said post being tapered down to said post above the patient's gum line, so as to leave a part of said post exposed between said gingival end of said crown analog and said gum line.

4. A combination according to claim 3 including pin means for fixing said crown analog on said post, said pin means extending between two opposite buccal and lingual side walls of said crown analog and through said post between them.

5. A combination according to claim 2 in which said abutment post has aperture means intermediate its ends providing a transverse passage across said post, said crown analog having apertures in its sidewalls which register with said passage when said crown analog is fitted over said supragingival end of said post, and pin means fitted through said apertures and said passage to fix said crown analog on said post.

6. A combination according to claim 5 in which said abutment post includes means at said gingival end to interlock with said implant fixture to prevent rotation of said post around its axis relative to said implant fixture.

7. A combination according to claim 2 for use with an implant fixture having an internally-threaded receiving bore in which said abutment post has a substantially axial tubular passage having at said gingival end an internal flange providing a shoulder for the head of a bolt by which to affix said post to said implant fixture.

8. A dental crown analog according to claim 2 in which said abutment post includes means at said gingival end to interlock with said implant fixture to prevent rotation of said post around its axis relative to said implant fixture.

9. A dental crown analog according to claim 2 in which said crown analog has an exterior surface material that is adapted to bond with an adhesive used to affix orthodontic anchoring devices to natural teeth.

10. A dental crown analog according to claim 1 for use with an implant fixture having an internally-threaded receiving bore, said analog including a generally axial tubular passage having at said gingival end an internal flange providing a shoulder for the head of a bolt by which to affix said analog to said implant fixture.

11. A dental crown analog according to claim 1 including means at its gingival end to cooperate with said implant fixture to prevent rotation of said analog around said implant fixture.

12. A dental crown analog according to claim 1 in which said crown analog has an exterior surface material that is adapted to bond with an adhesive used to affix orthodontic anchoring devices to natural teeth.

13. For use in the mouth of a patient having a dental implant fixture installed at an edentulous site, the combination of a prefabricated dental crown analog having exterior size and contour to approximate the dimensions and shape of a natural tooth at said site, and hollow tubular means providing an integral passage extending mesially-distally through said analog closer to one of the exterior buccal or lingual surfaces than to the center thereof for passage of an orthodontic wire therethrough, an abutment post adapted to be fixed at a gingival end to said implant fixture so as to extend supragingivally from said implant fixture, said analog having a bore opening through its gingival end sized for receiving said post therein, and means traversing said post intermediate its ends for interlocking said post with a side-wall of said analog to fix said analog over said post.

14. A dental crown analog according to claim 13 in which said abutment post includes means at said gingival end to interlock with said implant fixture to prevent rotation of said post relative to said implant fixture around the axis of said post.

15. A combination according to claim 13 in which said abutment post has a substantially axial passage having at said gingival end means to affix said post to said implant fixture, and aperture means in its walls intermediate its ends providing a transverse passage across said axial passage, said analog having apertures in its buccal and lingual sidewalls which register with said transverse passage when said crown analog is fitted over said post, and pin means fitted through said apertures and said transverse passage fixes said analog on said post.

16. A combination according to claim 13 in which said abutment post has aperture means intermediate its ends providing a transverse passage across said post, and said analog has apertures in its buccal and lingual sidewalls which register with said transverse passage when said crown analog is fitted over said post, and pin means fitted through said apertures and said transverse passage fixes said analog on said post.

* * * * *